United States Patent
Honkanen et al.

(10) Patent No.: US 8,811,704 B2
(45) Date of Patent: Aug. 19, 2014

(54) METHOD OF AND SYSTEM FOR ENHANCED DYNAMIC RANGE ASSAY ANALYSIS

(75) Inventors: Peter Honkanen, Concord, MA (US); Scott Douglas, Exeter, RI (US); Ralph H. Jung, Jr., Centennial, CO (US)

(73) Assignee: Aushon Biosystems, Inc., Billerica, MA (US)

( * ) Notice: Subject to any disclaimer, the term of this patent is extended or adjusted under 35 U.S.C. 154(b) by 0 days.

(21) Appl. No.: 13/439,643

(22) Filed: Apr. 4, 2012

(65) Prior Publication Data

US 2013/0034284 A1 Feb. 7, 2013

Related U.S. Application Data

(60) Provisional application No. 61/471,523, filed on Apr. 4, 2011.

(51) Int. Cl.
*G06K 9/00* (2006.01)
(52) U.S. Cl.
USPC .......................................................... 382/129
(58) Field of Classification Search
None
See application file for complete search history.

(56) References Cited

U.S. PATENT DOCUMENTS

| 7,361,472 | B2 | 4/2008 | Yguerabide et al. |
| 2003/0096302 | A1 | 5/2003 | Yguerabide et al. |
| 2007/0061880 | A1 | 3/2007 | Depta |
| 2008/0240543 | A1 | 10/2008 | Budach et al. |
| 2012/0071342 | A1* | 3/2012 | Lochhead et al. ............ 506/9 |
| 2013/0115606 | A1* | 5/2013 | Hansen et al. ............ 435/6.12 |

OTHER PUBLICATIONS

International Search Report issued for PCT/US12/032191, dated Jul. 11, 2012 (2 pages).

* cited by examiner

*Primary Examiner* — Atiba O Fitzpatrick
(74) *Attorney, Agent, or Firm* — Wilmer Cutler Pickering Hale and Dorr LLP

(57) ABSTRACT

The disclosed systems and methods allow composite images with enhanced dynamic range to be generated that result in more accurate, reliable, and efficient chemical and/or biological analyses. The disclosed systems include an image detector; a timer for tracking exposure time of the image detector; and computer readable medium, including instructions that when executed cause a computer system to generate a composite image using the multiple images of pixels.

10 Claims, 8 Drawing Sheets

|    | 32 | 33 | 34 | 35 | 36 | 37 | 38 | 39 | 40 | 41 | 42 | 43 |
|----|----|----|----|----|----|----|----|----|----|----|----|----|
| 32 | 221 | 336 | 311 | 389 | 394 | 409 | 345 | 407 | 285 | 186 | 153 | 124 |
| 33 | 371 | 342 | 363 | 473 | 498 | 472 | 552 | 498 | 354 | 248 | 153 | 141 |
| 34 | 343 | 358 | 405 | 600 | 761 | 856 | 826 | 707 | 545 | 361 | 175 | 163 |
| 35 | 370 | 423 | 610 | 839 | 1252 | 1436 | 1522 | 1482 | 1114 | 583 | 399 | 248 |
| 36 | 461 | 631 | 869 | 1250 | 1795 | 2592 | 3084 | 3002 | 2270 | 1242 | 1234 | 380 |
| 37 | 571 | 835 | 1117 | 1878 | 3423 | 6826 | 11713 | 11966 | 6879 | 2974 | 1899 | 538 |
| 38 | 833 | 3052 | 2552 | 3249 | 9445 | 80455 | 185483 | 178463 | 84675 | 11741 | 2734 | 837 |
| 39 | 1123 | 7450 | 7640 | 10354 | 56172 | 250534 | 178477 | 145153 | 238119 | 115090 | 6221 | 1405 |
| 40 | 7854 | 2447 | 2362 | 11302 | 134402 | 209524 | 138114 | 199623 | 265021 | 228579 | 15253 | 2539 |
| 41 | 24725 | 9756 | 7323 | 18554 | 143851 | 105346 | 172940 | 248090 | 249825 | 197965 | 45342 | 17290 |
| 42 | 2274 | 3062 | 4712 | 4906 | 34343 | 140828 | 244987 | 245210 | 227491 | 85654 | 27500 | 39586 |
| 43 | 696 | 881 | 1032 | 1441 | 4902 | 42012 | 125813 | 133532 | 65259 | 9006 | 3927 | 7586 |
| 44 | 1122 | 3563 | 4736 | 1075 | 1724 | 9573 | 12883 | 6470 | 4583 | 2699 | 1690 | 4937 |
| 45 | 682 | 4748 | 15931 | 4233 | 1023 | 1193 | 1708 | 1637 | 1579 | 1331 | 2739 | 5378 |
| 46 | 419 | 625 | 1320 | 9822 | 891 | 673 | 866 | 978 | 1064 | 728 | 1754 | 5082 |
| 47 | 221 | 310 | 327 | 435 | 450 | 453 | 522 | 646 | 480 | 341 | 380 | 1539 |
| 48 | 130 | 139 | 171 | 249 | 301 | 535 | 797 | 2908 | 565 | 382 | 200 | 194 |
| 49 | 82 | 117 | 199 | 302 | 260 | 565 | 908 | 1342 | 368 | 318 | 254 | 182 |
| 50 | 96 | 70 | 141 | 256 | 215 | 433 | 779 | 2254 | 273 | 164 | 196 | 171 |
| 51 | 70 | 69 | 75 | 92 | 161 | 189 | 511 | 5765 | 838 | 139 | 161 | 134 |
| 52 | 80 | 28 | 47 | 71 | 120 | 125 | 224 | 817 | 341 | 150 | 88 | 235 |
| 53 | 57 | 44 | 74 | 48 | 93 | 110 | 130 | 151 | 131 | 111 | 129 | 203 |
| 54 | 63 | 61 | 55 | 65 | 70 | 110 | 69 | 121 | 132 | 73 | 130 | 401 |
| 55 | 67 | 55 | 42 | 71 | 106 | 114 | 93 | 70 | 56 | 112 | 224 | 613 |
| 56 | 72 | 89 | 92 | 77 | 77 | 133 | 106 | 101 | 111 | 201 | 420 | 904 |
| 57 | 15 | 51 | 24 | 82 | 125 | 95 | 147 | 114 | 196 | 461 | 926 | 965 |
| 58 | 30 | 51 | 64 | 113 | 94 | 186 | 194 | 200 | 316 | 873 | 1174 | 738 |
| 59 | 75 | 270 | 220 | 111 | 212 | 278 | 334 | 360 | 707 | 1535 | 1682 | 930 |
| 60 | 132 | 289 | 287 | 172 | 285 | 514 | 611 | 694 | 1464 | 2607 | 1888 | 934 |
| 61 | 119 | 163 | 214 | 371 | 662 | 1112 | 1457 | 2061 | 3368 | 3242 | 2126 | 2495 |
| 62 | 81 | 189 | 353 | 777 | 2253 | 3910 | 6320 | 7519 | 6561 | 3993 | 2600 | 3055 |
| 63 | 150 | 340 | 670 | 2428 | 5586 | 33645 | 70416 | 67612 | 31167 | 6585 | 2266 | 2023 |
| 64 | 231 | 404 | 1387 | 4366 | 23280 | 101934 | 96477 | 87793 | 80032 | 28248 | 2609 | 1248 |
| 65 | 188 | 452 | 1640 | 6586 | 41318 | 80341 | 84328 | 83235 | 82660 | 54169 | 3290 | 475 |
| 66 | 143 | 438 | 1195 | 2920 | 27093 | 47147 | 53683 | 81324 | 83758 | 54136 | 5188 | 452 |
| 67 | 186 | 395 | 1040 | 2883 | 17173 | 67203 | 65796 | 83468 | 79533 | 23003 | 2147 | 393 |
| 68 | 171 | 534 | 1420 | 2285 | 5532 | 19748 | 36893 | 37343 | 26528 | 3803 | 589 | 247 |
| 69 | 236 | 562 | 834 | 992 | 1160 | 1747 | 2083 | 2024 | 1825 | 1008 | 267 | 181 |
| 70 | 395 | 552 | 785 | 902 | 921 | 1054 | 1066 | 826 | 599 | 314 | 203 | 134 |
| 71 | 764 | 763 | 690 | 721 | 461 | 468 | 721 | 469 | 317 | 144 | 127 | 81 |
| 72 | 645 | 388 | 203 | 374 | 734 | 456 | 546 | 228 | 183 | 42 | 51 | 46 |
| 73 | 407 | 2603 | 336 | 274 | 473 | 407 | 174 | 135 | 155 | 53 | 27 | 68 |
| 74 | 329 | 3844 | 438 | 391 | 222 | 165 | 115 | 96 | 67 | 41 | 42 | 18 |

| 44 | 45 | 46 | 47 | 48 | 49 | 50 | 51 | 52 | 53 | 54 | 55 | 56 | 57 | 58 | 59 | 60 | 61 |
|---|---|---|---|---|---|---|---|---|---|---|---|---|---|---|---|---|---|
| 98 | 119 | 250 | 9404 | 1552 | 147 | 35 | 37 | 21 | 23 | 45 | 13 | 63 | 25 | 36 | 58 | 23 | 39 |
| 111 | 107 | 245 | 5595 | 1902 | 137 | 32 | 45 | 25 | 47 | 0 | 64 | 19 | 9 | 34 | 32 | 56 | 24 |
| 145 | 100 | 169 | 184 | 146 | 61 | 27 | 60 | 4 | 32 | 51 | 47 | 52 | 25 | 31 | 40 | 5 | 81 |
| 171 | 77 | 93 | 136 | 89 | 58 | 52 | 56 | 35 | 31 | 24 | 58 | 47 | 57 | 31 | 55 | 52 | 124 |
| 252 | 126 | 117 | 95 | 107 | 77 | 42 | 34 | 2 | 30 | 31 | 52 | 39 | 39 | 68 | 46 | 96 | 270 |
| 218 | 202 | 77 | 110 | 82 | 69 | 44 | 4 | 65 | 17 | 75 | 1 | 44 | 48 | 59 | 75 | 291 | 1548 |
| 382 | 243 | 170 | 150 | 58 | 79 | 42 | 48 | 44 | 42 | 41 | 36 | 43 | 34 | 59 | 121 | 538 | 15090 |
| 569 | 313 | 188 | 116 | 148 | 151 | 59 | 32 | 45 | 27 | 0 | 39 | 25 | 59 | 99 | 240 | 699 | 9433 |
| 901 | 419 | 264 | 168 | 166 | 148 | 208 | 118 | 38 | 81 | 44 | 48 | 1209 | 46 | 109 | 379 | 1180 | 19558 |
| 2029 | 597 | 323 | 148 | 117 | 113 | 74 | 55 | 84 | 83 | 43 | 5 | 63 | 111 | 132 | 391 | 1109 | 19647 |
| 29677 | 1083 | 338 | 205 | 97 | 103 | 96 | 51 | 78 | 63 | 65 | 61 | 69 | 82 | 119 | 217 | 828 | 10493 |
| 6321 | 1459 | 384 | 150 | 64 | 108 | 71 | 109 | 65 | 106 | 80 | 78 | 50 | 88 | 105 | 190 | 624 | 1177 |
| 5973 | 6025 | 733 | 226 | 123 | 84 | 94 | 107 | 86 | 94 | 80 | 126 | 93 | 87 | 121 | 197 | 786 | 1087 |
| 6307 | 6911 | 2049 | 399 | 181 | 81 | 82 | 117 | 76 | 71 | 52 | 43 | 69 | 48 | 69 | 198 | 800 | 1101 |
| 6607 | 3647 | 1141 | 839 | 182 | 123 | 87 | 147 | 131 | 104 | 84 | 72 | 59 | 62 | 70 | 144 | 493 | 1088 |
| 1764 | 633 | 264 | 192 | 177 | 116 | 119 | 145 | 100 | 93 | 76 | 74 | 64 | 148 | 110 | 177 | 193 | 352 |
| 184 | 216 | 159 | 182 | 104 | 154 | 153 | 82 | 134 | 59 | 116 | 154 | 146 | 188 | 116 | 150 | 157 | 122 |
| 210 | 157 | 176 | 123 | 135 | 194 | 130 | 102 | 92 | 122 | 131 | 121 | 146 | 111 | 76 | 90 | 68 | 120 |
| 136 | 136 | 113 | 171 | 226 | 218 | 220 | 162 | 145 | 100 | 128 | 125 | 60 | 58 | 46 | 76 | 63 | 75 |
| 157 | 188 | 252 | 380 | 356 | 284 | 173 | 168 | 150 | 132 | 77 | 59 | 92 | 9 | 35 | 47 | 86 | 54 |
| 350 | 343 | 267 | 222 | 193 | 195 | 92 | 82 | 87 | 80 | 46 | 52 | 48 | 49 | 81 | 60 | 31 | 63 |
| 517 | 345 | 232 | 149 | 114 | 111 | 94 | 99 | 82 | 51 | 41 | 94 | 23 | 42 | 8 | 63 | 60 | 41 |
| 586 | 219 | 203 | 245 | 145 | 128 | 86 | 79 | 22 | 20 | 54 | 86 | 27 | 52 | 47 | 26 | 53 | 46 |
| 665 | 295 | 203 | 173 | 109 | 109 | 80 | 78 | 46 | 45 | 72 | 45 | 42 | 40 | 33 | 40 | 32 | 75 |
| 679 | 338 | 250 | 233 | 122 | 88 | 80 | 105 | 53 | 55 | 98 | 64 | 40 | 111 | 76 | 47 | 63 | 73 |
| 483 | 344 | 349 | 274 | 121 | 101 | 26 | 114 | 86 | 83 | 104 | 79 | 52 | 106 | 83 | 86 | 116 | 132 |
| 336 | 416 | 377 | 199 | 150 | 77 | 70 | 60 | 76 | 86 | 118 | 163 | 124 | 124 | 84 | 147 | 156 | 183 |
| 461 | 391 | 274 | 149 | 63 | 64 | 31 | 49 | 89 | 86 | 109 | 68 | 139 | 99 | 128 | 172 | 198 | 285 |
| 681 | 401 | 171 | 69 | 67 | 47 | 103 | 53 | 87 | 26 | 36 | 82 | 167 | 206 | 190 | 275 | 376 | 608 |
| 2034 | 724 | 191 | 81 | 88 | 41 | 47 | 0 | 44 | 78 | 63 | 99 | 133 | 268 | 289 | 491 | 1022 | 2244 |
| 2729 | 1653 | 206 | 78 | 60 | 71 | 35 | 54 | 46 | 38 | 47 | 35 | 89 | 170 | 327 | 849 | 2897 | 4728 |
| 2464 | 1958 | 275 | 69 | 68 | 16 | 53 | 50 | 47 | 69 | 41 | 44 | 108 | 187 | 374 | 1093 | 5040 | 8517 |
| 1650 | 1065 | 110 | 22 | 39 | 68 | 91 | 58 | 50 | 41 | 52 | 56 | 99 | 176 | 341 | 1428 | 8439 | 25644 |
| 231 | 150 | 103 | 92 | 49 | 80 | 70 | 53 | 48 | 39 | 36 | 45 | 79 | 170 | 338 | 1119 | 5391 | 63358 |
| 172 | 78 | 72 | 52 | 26 | 29 | 54 | 45 | 67 | 53 | 32 | 20 | 130 | 485 | 377 | 942 | 3699 | 60924 |
| 171 | 126 | 76 | 11 | 52 | 37 | 38 | 35 | 81 | 19 | 26 | 21 | 81 | 1139 | 651 | 1001 | 2117 | 21893 |
| 97 | 104 | 43 | 9 | 44 | 52 | 39 | 42 | 16 | 28 | 82 | 17 | 94 | 187 | 591 | 777 | 900 | 3307 |
| 106 | 73 | 26 | 47 | 56 | 26 | 39 | 32 | 8 | 3 | 27 | 45 | 46 | 121 | 265 | 343 | 346 | 868 |
| 81 | 84 | 66 | 38 | 37 | 36 | 26 | 22 | 8 | 24 | 35 | 29 | 64 | 81 | 98 | 129 | 209 | 374 |
| 104 | 44 | 35 | 51 | 33 | 38 | 29 | 58 | 65 | 47 | 34 | 26 | 35 | 30 | 98 | 96 | 115 | 230 |
| 60 | 32 | 60 | 33 | 45 | 45 | 32 | 32 | 16 | 60 | 18 | 45 | 33 | 46 | 79 | 72 | 96 | 160 |
| 25 | 18 | 50 | 38 | 1 | 42 | 28 | 77 | 24 | 5 | 26 | 56 | 17 | 35 | 46 | 70 | 56 | 117 |
| 76 | 33 | 26 | 4 | 33 | 41 | 2 | 10 | 62 | 87 | 33 | 19 | 25 | 48 | 20 | 43 | 51 | 111 |

FIG. 3B

| 62 | 63 | 64 | 65 | 66 | 67 | 68 | 69 | 70 | 71 | 72 | 73 | 74 |
|---|---|---|---|---|---|---|---|---|---|---|---|---|
| 66 | 60 | 87 | 50 | 72 | 143 | 137 | 142 | 127 | 146 | 162 | 93 | 141 |
| 96 | 73 | 78 | 105 | 116 | 118 | 104 | 153 | 162 | 116 | 111 | 72 | 70 |
| 95 | 124 | 91 | 103 | 143 | 98 | 77 | 107 | 144 | 114 | 103 | 82 | 75 |
| 150 | 195 | 128 | 106 | 141 | 110 | 119 | 159 | 107 | 64 | 130 | 95 | 45 |
| 286 | 296 | 265 | 187 | 118 | 87 | 109 | 54 | 89 | 81 | 128 | 77 | 53 |
| 1277 | 1245 | 763 | 419 | 255 | 171 | 121 | 92 | 69 | 82 | 123 | 53 | 38 |
| 18778 | 15794 | 9353 | 3109 | 655 | 232 | 150 | 45 | 56 | 61 | 102 | 54 | 67 |
| 32131 | 32899 | 22042 | 14488 | 6927 | 498 | 181 | 120 | 80 | 36 | 26 | 71 | 74 |
| 33123 | 37159 | 36644 | 27416 | 15573 | 758 | 188 | 92 | 67 | 53 | 53 | 64 | 56 |
| 33697 | 37004 | 41068 | 44229 | 19710 | 594 | 205 | 78 | 70 | 67 | 43 | 63 | 56 |
| 31131 | 37227 | 42322 | 40739 | 5924 | 416 | 129 | 95 | 70 | 27 | 20 | 13 | 32 |
| 8226 | 21630 | 22137 | 7188 | 830 | 194 | 123 | 78 | 84 | 52 | 27 | 66 | 33 |
| 989 | 1089 | 947 | 588 | 272 | 100 | 105 | 62 | 32 | 26 | 38 | 30 | 56 |
| 1286 | 686 | 386 | 244 | 141 | 99 | 64 | 46 | 97 | 55 | 38 | 17 | 53 |
| 1205 | 496 | 218 | 170 | 103 | 90 | 201 | 185 | 78 | 70 | 0 | 19 | 30 |
| 307 | 231 | 166 | 140 | 103 | 31 | 58 | 48 | 46 | 40 | 35 | 9 | 33 |
| 150 | 143 | 159 | 111 | 35 | 24 | 51 | 43 | 57 | 25 | 58 | 46 | 60 |
| 82 | 114 | 107 | 38 | 45 | 44 | 23 | 36 | 40 | 10 | 44 | 33 | 32 |
| 69 | 70 | 80 | 26 | 46 | 2 | 26 | 49 | 40 | 14 | 13 | 6 | 39 |
| 83 | 60 | 59 | 27 | 35 | 43 | 35 | 25 | 12 | 21 | 11 | 8 | 35 |
| 76 | 50 | 44 | 42 | 51 | 43 | 14 | 10 | 46 | 27 | 28 | 13 | 21 |
| 77 | 68 | 78 | 31 | 58 | 59 | 24 | 18 | 21 | 61 | 28 | 5 | 38 |
| 105 | 126 | 56 | 98 | 85 | 47 | 33 | 66 | 40 | 31 | 15 | 45 | 37 |
| 97 | 146 | 66 | 72 | 48 | 6 | 30 | 5 | 11 | 25 | 62 | 41 | 0 |
| 133 | 109 | 123 | 98 | 51 | 41 | 28 | 40 | 33 | 51 | 12 | 13 | 64 |
| 139 | 169 | 166 | 105 | 86 | 3 | 5 | 30 | 67 | 20 | 22 | 32 | 35 |
| 219 | 253 | 210 | 189 | 98 | 56 | 92 | 42 | 41 | 28 | 22 | 35 | 19 |
| 363 | 365 | 341 | 161 | 88 | 96 | 80 | 84 | 56 | 61 | 34 | 43 | 19 |
| 721 | 786 | 683 | 451 | 271 | 135 | 100 | 82 | 35 | 54 | 0 | 21 | 43 |
| 2861 | 2386 | 1537 | 1043 | 483 | 291 | 130 | 101 | 60 | 66 | 58 | 54 | 27 |
| 6526 | 9419 | 7865 | 6367 | 2166 | 524 | 200 | 99 | 86 | 56 | 51 | 11 | 47 |
| 22136 | 50813 | 57722 | 41518 | 9344 | 796 | 232 | 153 | 89 | 53 | 42 | 49 | 76 |
| 91871 | 102057 | 99952 | 103464 | 39877 | 2309 | 472 | 214 | 91 | 61 | 26 | 23 | 37 |
| 111202 | 106630 | 108369 | 110936 | 77261 | 3813 | 568 | 266 | 97 | 92 | 43 | 43 | 66 |
| 120941 | 112657 | 112500 | 114292 | 63729 | 3833 | 569 | 161 | 121 | 83 | 36 | 26 | 45 |
| 116393 | 126393 | 122833 | 104519 | 27975 | 1867 | 463 | 206 | 139 | 107 | 3 | 47 | 29 |
| 23478 | 75939 | 85635 | 29376 | 3994 | 763 | 443 | 191 | 136 | 99 | 48 | 57 | 59 |
| 2248 | 4087 | 7192 | 2652 | 3348 | 343 | 315 | 219 | 139 | 61 | 96 | 67 | 42 |
| 1210 | 3038 | 891 | 631 | 361 | 274 | 318 | 171 | 85 | 64 | 74 | 88 | 48 |
| 536 | 1194 | 449 | 275 | 290 | 1944 | 365 | 84 | 38 | 90 | 78 | 21 | 38 |
| 256 | 286 | 216 | 232 | 251 | 2321 | 249 | 60 | 130 | 122 | 71 | 35 | 20 |
| 134 | 112 | 147 | 162 | 122 | 97 | 76 | 122 | 134 | 52 | 54 | 44 | 87 |
| 74 | 143 | 122 | 55 | 78 | 108 | 123 | 114 | 56 | 62 | 55 | 68 | 98 |

| Spot | Avg Intensity |
|---|---|
| 1 | 160970 |
| 2 | 23651 |
| 3 | 57827 |
| 4 | 79134 |

FIG. 3C

METHOD OF AND SYSTEM FOR ENHANCED DYNAMIC RANGE ASSAY ANALYSIS

CROSS REFERENCE TO RELATED APPLICATIONS

This application claims the benefit of U.S. Provisional Application No. 61/471,523, filed Apr. 4, 2011, the entire contents of which are hereby incorporated by reference herein.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

1. Field of Disclosure

The present disclosure relates to assay analysis, and, more specifically, to methods and systems for analyzing assay results using enhanced dynamic ranges.

2. Description of Related Art

Antibody-based immunoassays are used for applications such as biomarker verification or validation. One modern medical diagnostic testing technique is an enzyme-linked immunosorbent assay (ELISA). Generally, in an ELISA, a capture antibody is printed in the bottom of a reaction well in an assay substrate. An assay substrate is a surface upon which various chemical and/or biological analyses can be performed. Examples of an assay substrate include microarray plates, glass slides, and microtiter plates. A microtiter plate is a flat plate that has multiple "wells" formed in its surface. Each reaction well can be used as a small test tube into which various materials can be placed to perform biochemical analyses.

In an ELISA, the capture antibody has specificity for a particular antigen for which the assay is being performed. A sample to be analyzed is added to the well containing the capture antibody, and the capture antibody "captures" or immobilizes the antigen contained in the sample. A detect antibody is then added to the well, which also binds and/or forms a complex with the antigen. Further materials are then added to the well that cause a detectable signal to be produced by the detect antibody. For example, when light of a specific wavelength is shone upon the well, the antigen/antibody complexes will fluoresce. The amount of antigen in the sample can be inferred based on the magnitude of the fluorescence. In another example, a compound can be added to the well that causes the detect antibody to emit light within a predetermined wavelength (e.g., 400-500 nm) when properly energized by a suitable source. This light can be read by an optical detector, such as a charged-coupled device (CCD) camera or CMOS sensors, to measure the optical brightness or intensity of the emitted light. During an ELISA, the absorbency, fluorescence, or electrochemical signal of the well can be measured with suitable detection and processing equipment and compared with a standard to determine the presence and quantity of the sample antigen.

Assay performance involves the ability of the assay to precisely and accurately detect analytes in the sample. A singleplex immunoassay quantifies one analyte per assay, while a multiplex assay simultaneously measures multiple analytes in a single assay. Multiplex assays are used, for example, in functional genomics experiments that detect the presence of biomolecules of a given class (e.g., mRNAs, proteins) within a biological sample.

Factors that can influence the accuracy of assay detection include antibody pairs, binding between antibody and capture surface, signal amplification, and range of signal linearity detection. Because more variables are involved with multiplex assays as compared to singleplex assays, multiplex assays can be more prone to error. For example, cross-reactivity can occur in multiplex wells, as multiple pairs of capture antibodies and detectors are mixed in a single reaction well. Both pre-analytical error, for example, sample degradation or matrix heterogeneity, and analytical error can affect the accuracy and reliability of the detection signal.

SUMMARY

The disclosed systems and methods allow composite images with enhanced dynamic range to be generated that result in more accurate, reliable, and efficient chemical and/or biological analyses.

In one aspect, the disclosed methods comprise (a) obtaining multiple images of pixels representing light intensity output from an assay, wherein the light intensity output indicates a presence and an amount of a substance within wells of a test plate, and wherein the multiple images of pixels are generated by using a detector to detect the light intensity of the pixels of the wells using a standard exposure time; and a longer-than-standard exposure time; and (b) generating a composite image using the multiple images of pixels, including: determining an exposure compensation ratio based on the standard exposure time and the longer-than-standard exposure time; determining a presence of out-of-range pixels in the image that used the longer-than-standard exposure time, wherein the out-of-range pixels have light intensities that exceed a threshold based on a maximum capacity of the detector; placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio; determining a presence of in-range pixels in the image that used a longer-than-standard exposure time, wherein the in-range pixels have light intensities that are below the threshold; and placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

In one or more embodiments, the method further comprises using the composite image to determine the presence and the amount of the substance within the wells.

In one or more embodiments, the longer-than-standard exposure time in the disclosed methods is about 2 to about 10 times the standard exposure time.

In one or more embodiments, the methods further comprise applying an image calibration procedure to the multiple images of pixels generated in step (a), wherein the image calibration procedure includes subtracting dark noise and applying flat field correction.

In one or more embodiments, the methods further comprise obtaining one or more of the composite images; combining the pixels in one or more of the composite images with pixels at a same relative position in other composite images to generate a template image of the wells, wherein the composite pixels at the same relative positions represent anticipated positions of printed features in a test plate; and using the template image to find a location of a feature within the test plate, wherein the location indicates presence and amount of a substance in the test plate.

In one aspect, the disclosed methods comprise obtaining multiple pixel images representing light intensity output from one or more assays, wherein the wells include features printed in the wells of a testing substrate; combining the multiple pixel images with pixels at a same relative position in other images to generate a template image of the wells, wherein pixels of the template image at the same relative positions represent anticipated positions of printed features in a test plate; and using the template image to find a location of a feature within the test plate, wherein the location indicates a presence and an amount of a substance in the test plate.

In one aspect, the disclosed systems comprise an image detector; a timer for tracking exposure time of the image detector; and computer readable medium, including instructions that when executed cause a computer system to generate a composite image using the multiple images of pixels by: (a) obtaining multiple images of pixels representing light intensity output from an assay, wherein the light intensity output indicates a presence and an amount of a substance within wells of a test plate, and wherein the multiple images of pixels are generated by using a detector to detect the light intensity of the pixels of the wells using a standard exposure time; and a longer-than-standard exposure time; and (b) generating a composite image using the multiple images of pixels, including:
  determining an exposure compensation ratio based on the standard exposure time and the longer-than-standard exposure time;
  determining a presence of out-of-range pixels in the image that used the longer-than-standard exposure time, wherein the out-of-range pixels have light intensities that exceed a threshold based on a maximum capacity of the detector;
  placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio;
  determining a presence of in-range pixels in the image that used a longer-than-standard exposure time, wherein the in-range pixels have light intensities that are below the threshold; and
  placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

In one or more embodiments, the composite image in the systems is used to determine the presence and amount of the substance within the wells.

In one or more embodiments, the longer-than-standard exposure time in the systems is about 2 to about 10 times the standard exposure time.

In one or more embodiments, the multiple images of pixels in the systems are processed using a calibration procedure, including subtracting dark noise and applying flat field correction.

DETAILED DESCRIPTION

Figure 1:
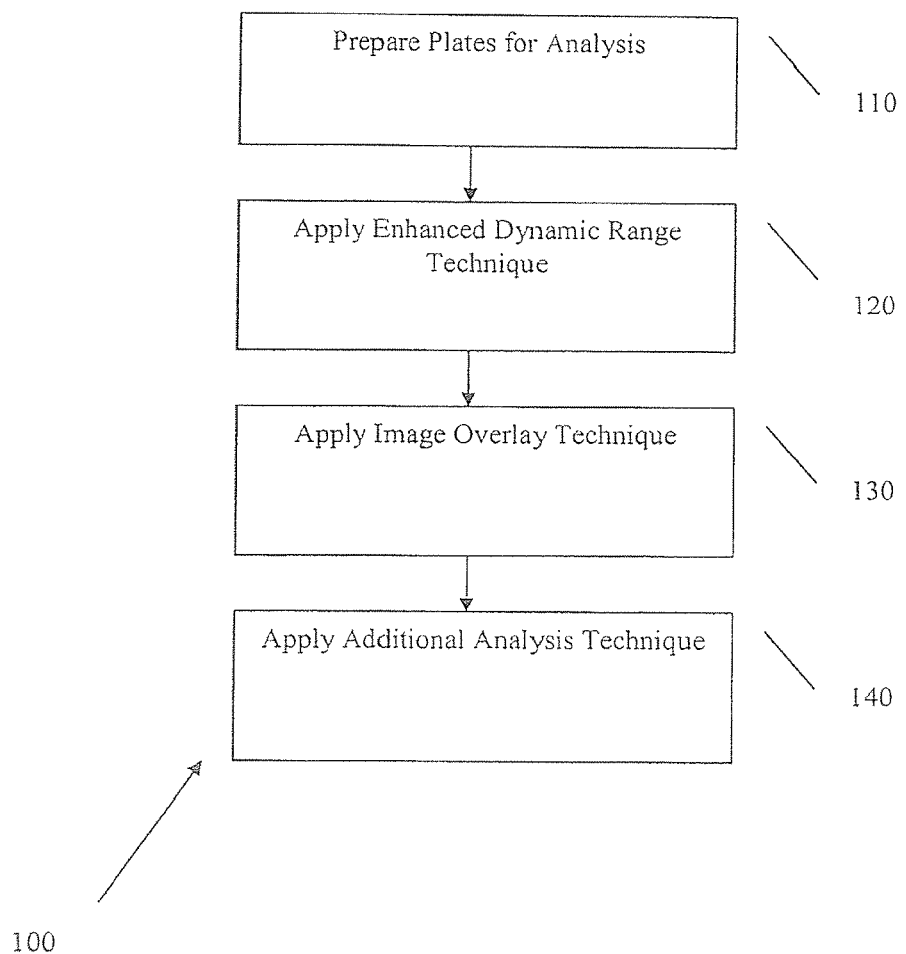
FIG. 1 is a flow chart depicting a method of enhancing the dynamic range during assay analysis.

In one illustrative embodiment, method 100 increases the detection capabilities of a biochemical assay by enhancing the dynamic range of assay results. The method also increases assay throughput and reduces processing time for running experiments and analyses, as fewer assays must be run because of the enhanced dynamic range. The reduction in the number of assays that must be run reduces or eliminates the inaccuracy that can result from signal variability and day-to-day variability. Embodiments described herein increase the throughput and efficiency of all biochemical analyses (e.g., ELISAs) where the output signal is related to light intensity.

In one aspect, the disclosed methods comprise (a) obtaining multiple images of pixels representing light intensity output from an assay, wherein the light intensity output indicates a presence and an amount of a substance within wells of a test plate, and wherein the multiple images of pixels are generated by using a detector to detect the light intensity of the pixels of the wells using a standard exposure time; and a longer-than-standard exposure time; and (b) generating a composite image using the multiple images of pixels, including: determining an exposure compensation ratio based on the standard exposure time and the longer-than-standard exposure time; determining a presence of out-of-range pixels in the image that used the longer-than-standard exposure time, wherein the out-of-range pixels have light intensities that exceed a threshold based on a maximum capacity of the detector; placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio; determining a presence of in-range pixels in the image that used a longer-than-standard exposure time, wherein the in-range pixels have light intensities that are below the threshold; and placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

Suitable samples for use in assays and other biochemical analyses include proteomic samples from, for example, cell lysates, cell supernatants, plasma, serum, and other biological fluids.

Prepare the Plate for Image Analysis (Step 110)

In accordance with method 100, steps are taken to prepare the plate for image analysis (step 110). This preparation can include assay preparation steps known in the art. For example, during an ELISA, a capture antibody feature is printed onto the bottom of the well, and a blocking material is added to the well to block plate binding sites that remain on the plate. As used herein, "features" can have different shapes, such as, for example, a rounded shape. The features can be, for example, about 300 µm to about 500 µm in diameter. Blocking inhibits non-selective binding of sample antigens to the base of the well during the ELISA, which would give false readings. Second, an antigen-containing sample is added to the well. Third, the well is washed so that unbound antigen is removed. Fourth, enzyme-linked detect antibodies are added. The well is then washed so that unbound antibody-enzyme conjugates are removed. Next, a substance is applied to convert the enzyme into a detectable signal, such as a color, fluorescent, electrochemical, or chemiluminescent signal. The absorbency, fluorescence, electrochemical, or chemiluminescent signal of the well is measured with a suitable detection system, and a resulting signal compared in a processing system with a standard to determine the presence and quantity of the sample antigen.

The substance added to reaction wells to produce a detectable signal can be, for example, a SuperSignal chemiluminescent substrate (commercially available from Thermo Scientific). As mentioned above, the amount of light emitted by the various assay features corresponds to the amount of antibody captured by the assay. The plate is imaged using an image detector for a period of time in the range of seconds to determine the highest level of light signal output by any one feature. An image detector is a device that converts an optical image to an electric signal. For example, a charge coupled device (CCD) or a complementary metal-oxide-semiconductor (CMOS) active pixel sensor can be used. The image can be displayed, for example, on paper or a computer monitor.

In various embodiments, the plate is imaged for about 1, 2, 3, 4, 5, 6, 7, 8, 9, or 10 seconds. In one embodiment, the plate is imaged for about 4 seconds.

Next, image calibration procedures known in the art can be applied to the image. Common image calibration procedures include subtracting dark noise and applying flat field correction. Dark current is the relatively small electric current that flows through photosensitive devices, including a photomultiplier tube, photodiode, or CCD even when no photons are entering the device. Dark current is one of the main sources of noise in image sensors. Dark current is an additive source of signal, such that the number of counts in each pixel is the sum of thermal electrons and photoelectrons. To subtract the dark current, it is known in the art to make an estimate of the number of thermal electrons in a particular pixel and subtract that estimate from the measured number of electrons for the pixel.

Another image calibration procedure known in the art is flat-field correction. A flat-field consists of two numbers for each pixel—the pixel's gain and its dark current. The pixel's gain is how the amount of signal given by the detector varies as a function of the amount of light (or equivalent). The gain is usually a linear variable, and is described as the ratio of the input and output signals. The dark current is the amount of signal given out by the detector when there is no incident light. Flat field correction or "flat-fielding" removes artifacts from two-dimensional images that are caused by variations in the pixel-to-pixel sensitivity of the detector and/or by distortions in the optical path. Flat fielding compensates for different gains and dark currents in a detector. Once a detector has been appropriately flat-fielded, a uniform signal will create a more uniform output.

In one or more embodiments, a centroid search of grids within the plate wells is optionally used to locate the center of the features printed on a reaction well. A centroid is the geometric center of an object. Formulas and algorithms known in the art are used to perform this centroid search. In other embodiments, multiple centroid scans are performed to select the features within each expected feature configuration. For example, a 3×3 grid or a circle of features can be used in each well of the plate. The centroid search described herein eliminates or reduces background signal, such as signal from the outside of the wells. Performing one or more centroid searches thus increases the accuracy of signal output in assay results.

In one or more embodiments, the features are sorted from most intense pixel to lease intense pixel, or vice versa, and maximum pixel intensity within the wells is determined. Next, an exposure time is calculated that results in no pixels exceeding a threshold based on a maximum capacity of the detector. In some embodiments, the threshold is the maximum count capability of the camera used plus a preselected buffer count. As used herein, the "standard exposure time" is an exposure time that will result in no pixels exceeding the maximum count plus a buffer count. In one embodiment, if a 16-bit camera is used, then the maximum count is 65,536 ($2^{16}$). In some implementations, a standard exposure time is calculated such that no pixels exceed about 60,000 counts (providing a buffer of 5,536). In other embodiments, a standard exposure time is calculated such that no pixels exceed about 50,000 counts (providing a buffer of 15,536). Smaller or larger buffer counts can be used. Next, an image is developed using that standard exposure time.

Enhanced Dynamic Range Technique (Step 120)

In accordance with method 100 as shown in FIG. 1, steps are taken to apply an enhanced dynamic range technique (step 120). As described herein, photographic film or digital image sensors have a physically limited useful or optimal exposure range or dynamic range. For example, a CCD camera is limited by its bit count. Exposure is the total amount of light allowed to fall on the photographic medium (e.g., photographic film or image sensor) when taking a reading of the results. If any part of the image is outside the range, then the sensor cannot record the relative intensity data accurately. For example, out-of-range values can be recorded as black (under-exposed) or white (over-exposed) instead of shades of gray that more accurately depict the granularity and detail of the image.

The systems and methods described herein enhance the dynamic range of assay results such that biochemical analyses are more efficient, accurate, and reliable. In one embodiment, the systems and methods include capturing multiple exposures of an image, processing out-of-range values (for example, overexposed and underexposed portions of the image) based on a pixel evaluation, and generating a composite image with enhanced dynamic range. This composite image achieves a greater contrast range than the individual images used to form the composite image.

Figure 4:
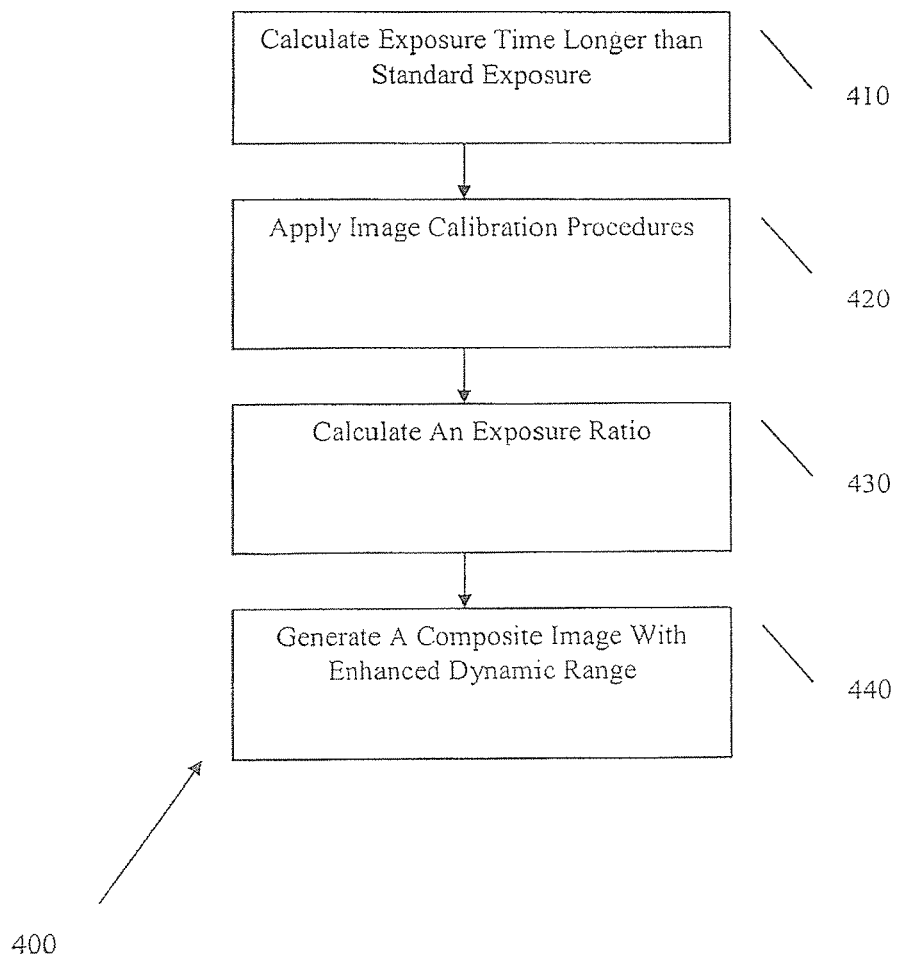
FIG. 4 is a flow chart depicting the sub-steps of step 120 as shown in FIG. 1.

FIG. 4 is a flow chart depicting the sub-steps of step 120 as shown in FIG. 1. In one embodiment, sub-step 410 is performed to calculate an exposure time longer than standard exposure. In one or more embodiments, a longer exposure time, e.g., ranging from about 2 to about 10 times the standard exposure time, is selected. In one embodiment, several exposures times, e.g., ranging from about 2 to about 10 times the standard exposure time, are selected. In another embodiment, the longer exposure time is about 5 times the standard exposure time. Next, one or more images are developed using the longer exposure time(s). The longer exposure time enables the detection of features that have a response that is too low to be reliably detected by the film or image sensor. In one embodiment, sub-step 420 is performed to apply image calibration procedures known in the art, such as but not limited to subtracting dark and applying flat field correction as described herein, to further calibrate the images.

In one embodiment, sub-step 430 is performed to determine an exposure compensation ratio based on the standard exposure time and the longer-than-standard exposure time to scale the out-of-range pixels. A signal decay ratio is used to adjust the pixels still in-range. The intensity difference caused by the difference in exposure time and the reduction due to the decay of the signal is determined. Intensity difference is linearly related to exposure time, and this relationship determines calculations for an exposure compensation ratio. Thus, a feature detected at a longer exposure that is five times greater than a standard exposure will have an intensity that is about five times greater. Pixels within a certain range in the standard exposure are selected and compared to the same pixels in the longer-than-standard exposure. In one embodiment, if a 16-bit camera was used to capture the images, then pixels within the range of about 5,000 to about 50,000 in the longer-than-standard exposure times are selected. Next, the average of the ratios between the pixels in the standard exposure and in the longer exposure is calculated as the observed exposure ratio. The observed exposure ratio is compared to the known exposure ratio to account for the signal decay. For example, if the longer exposure time is five times greater than the standard exposure time, and the observed exposure is only 4.5 greater than a standard exposure, then a multiplier of 1.1111 is used to account for the observed exposure ratio not being intense as it should be due to signal decay.

In one embodiment, sub-step 440 is performed to generate a composite image with enhanced dynamic range by examining each pixel in the longer exposure. In one aspect, if the longer exposure pixel exceeds the maximum bit capacity (potentially saturated before dark and flat file calibrations are applied), then the pixel is replaced with the standard exposure pixel at the same coordinates multiplied by the exposure and decay compensation ratios. In one embodiment, for a 16-bit camera, the maximum bit capacity is about 60,000. The resulting composite image is a floating point image with increased count values as compared to values using a standard exposure time. In one embodiment, using a 16-bit camera and a longer exposure time of 5 multiplied by the standard exposure time, the resulting composite image has values between about 0 and about 325,000.

Figure 2A:
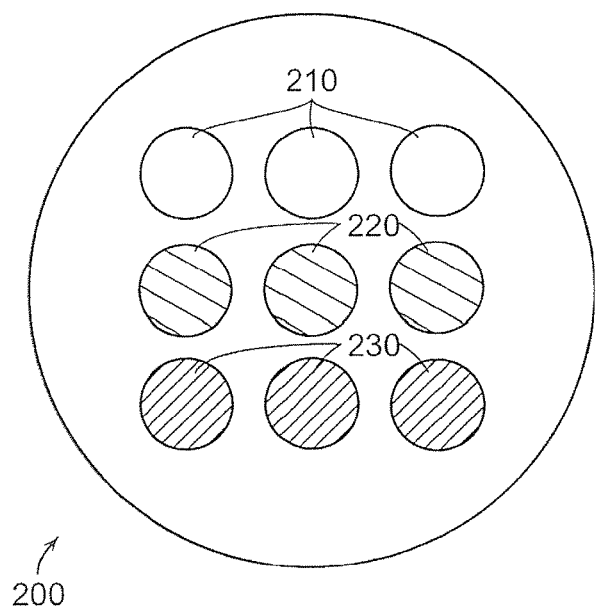
FIGS. 2A-C are depictions of assay image results in one reaction well of, for example, a 96-well microtiter plate.
Figure 2B:
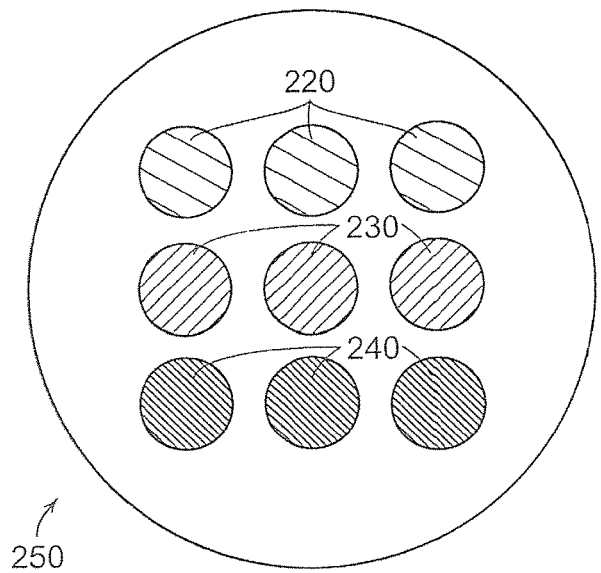
Figure 2C:
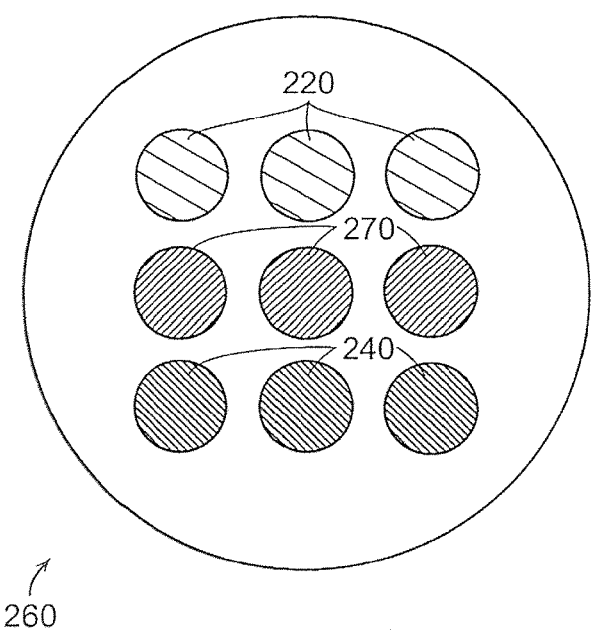

FIGS. 2A-C are depictions of assay image results in one reaction well of, for example, a 96-well plate. For ease of illustration, the depictions show a photonegative representation of a chemiluminescent response. Thus, in the depiction, the absence of signal is represented by white, and increasing levels of signal are represented by darkening shades of gray. However, in an actual assay image, the absence of a signal is represented by black, and increasing levels of signal are measured as increasingly lighter shades of gray. The signals depicted are i) not visible (feature 210), ii) dim (feature 220), iii) medium bright (feature 230), and iv) bright (feature 240).

FIG. 2A shows features or spots in a reaction well 200 that was imaged using a standard exposure time. FIG. 2C shows features in the same reaction well 260 that was imaged using a longer exposure time. Features 220 are medium bright, and features 240 are bright. However, because features 240 reached the maximum value of the camera bit capabilities, it is unknown whether the true count values of features 270 in FIG. 2C are, for example, 65,536, 80,000, or higher.

FIG. 2B shows a composite image of the same reaction well generated using the embodiments described herein. The composite image is formed after an image is generated using a longer exposure time (as depicted in FIG. 2C), and the images captured using multiple exposure times are processed based on pixel evaluation. In FIG. 2B, features 220 that were not visible in the same location using the standard exposure time are visible in the composite image. Features 270 in FIG. 2C exceeded the maximum bit capacity (potentially saturated before dark and flat file calibrations are applied), so the pixels were replaced with the standard exposure pixel at the same coordinates multiplied by the exposure compensation and decay ratios. Thus, features 230 of FIG. 2B are medium bright and accurately reflect their relative intensity values.

Figures 3, 3A:
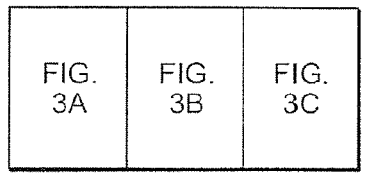
FIG. 3 is a chart showing pixel intensity results after a composite image is generated as described in certain embodiments.

FIG. 3 shows pixel intensities after generation of a composite image using the methods and systems described herein. Using a 16-bit camera, the composite image has values ranging between 0 and 325,000. The composite image allows the display of values that were below background in the standard exposure while retaining accurate relative intensity information for the pixels that were above the maximum measureable intensity in the longer exposure. Thus, pixel intensities that were over 60,000 in the longer exposure (potentially saturated before dark and flat field correction were applied) were replaced with the standard exposure pixels in the same regions after accounting for the exposure and decay differences caused by the time that elapsed between the standard exposure and the longer exposure.

In some embodiments, a processing system is used to perform the enhanced dynamic range techniques described herein. The processing system can include one or more processors or controllers, and can include one or more programmed general purpose processors, or one or more application-specific processors. The image detector and processor communicate via interfaces for the exchange of data by, for example, commonly accessible computer memory or by a network connection. In one embodiment the processor is part of a computer comprising a printed circuit board with the necessary components within the image detector. In some embodiments, a robotic system is used to perform the techniques described herein, and the robotic system comprises a computer, a drive system, and a image detector (e.g., a camera) with exposure control mechanisms. In some embodiments, a computer runs image processing algorithms to produce the enhanced dynamic range images described herein. In other embodiments, a human processes and analyzes the images using the embodiments described herein.

In one aspect, the systems comprise an image detector; a timer for tracking exposure time of the image detector; and computer readable medium, including instructions that when executed cause a computer system to generate a composite image using the multiple images of pixels by: (a) obtaining multiple images of pixels representing light intensity output from an assay, wherein the light intensity output indicates a presence and an amount of a substance within wells of a test plate, and wherein the multiple images of pixels are generated by using a detector to detect the light intensity of the pixels of the wells using a standard exposure time; and a longer-than-standard exposure time; and (b) generating a composite image using the multiple images of pixels, including: determining an exposure compensation ratio based on the standard exposure time and the longer-than-standard exposure time;

determining a presence of out-of-range pixels in the image that used the longer-than-standard exposure time, wherein the out-of-range pixels have light intensities that exceed a threshold based on a maximum capacity of the detector; placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio; determining a presence of in-range pixels in the image that used a longer-than-standard exposure time, wherein the in-range pixels have light intensities that are below the threshold; and placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

Software can be maintained on tangible memory devices, including optical, magnetic, or solid state memory, such that when executed, perform acts as described herein.

In display monitors and digital image output signals, the pixel is the smallest unit of an image. On a digital camera sensor, the pixels are arranged in a regular pattern. When light enters the camera lens, it travels onto the pixels that record the intensity of light at that particular location. Digital pixels are equivalent to the individual silver halide grains used in film photography. After the lens closes, the digital camera sensor encodes this intensity information by recording the light information from each signal. A light detector transfers the light intensity into a voltage reading. More light on a single pixel creates a larger charge, while areas of the image that do not reflect a lot of light build up a smaller charge. The charges can go through an analog-digital converter that transfers the charges into a digital signal. After the light signal is converted into a digital signal, the camera uses bit information to encode the digital signal with a format compatible with the computer. This information describes the intensity of the light.

Light detectors have an upper and lower threshold. First, sensors have a maximum charge capacity. After the maximum charge is reached, the sensor cannot increase its signal and cannot record additional light values. Thus, this limitation results in a point after which the sensor is unable to distinguish one intense light from another. Second, sensors also have a minimum charge capacity, which is the minimum charge that the sensor can convert to a digital encoding. Any pixel charge lower than this minimum threshold can only be encoded as pure black. The embodiments described herein enhance the dynamic range of light detectors and thus increases the detection range of assays and biochemical analyses whose output signal is related to light intensity.

The sensitivity of an assay is described by its lower limit of detection (LLOD) and lower limit of quantification (LLOQ). LLOD, also referred to as the minimum detectable dose, is the lowest concentration of analyte in a biological sample that an assay can reliably differentiate from background. LLOQ is the lowest amount of an analyte that can be quantified reproducibly with acceptable precision and accuracy. The upper limit of quantification (ULOQ) is the maximum analyte concentration of a sample that can be quantified with acceptable precision and accuracy. By enhancing the dynamic range of the assay images, the systems and methods described herein allow lower concentrations of analyte to be detectable and quantified, and higher concentrations of analyte to be more accurately quantified.

The systems and methods described here can thus provide enhanced dynamic range of the assay results and increase accuracy and reliability at the extreme ends of a calibration curve. In one embodiment, the enhanced dynamic range described herein increases the detection capabilities of an assay by increasing the range of the minimum detectable dose and maximum detectable dose. The systems and methods described here can reduce the number of times assays must be run, thus increasing the accuracy and reliability of assay results by reducing or eliminating the error caused by day-to-to-day variation of assay analysis. The disclosed systems and methods increase the throughput and efficiency of assays and other biochemical analyses and reduce processing time for running analyses and experiments.

Apply Image Overlay Technique (Step 130)

In accordance with method 100 shown in FIG. 1, an optional image overlay technique can be taken to further process image results (step 130). The image overlay technique can be used either on images generated with enhanced dynamic range, or on images that have not been generated with enhanced dynamic range. The systems and methods described in step 130 generate an overlay template image to more accurately and efficiently identify and locate features that show the presence of an analyte in a biochemical analysis.

In one or more embodiments, the methods comprise obtaining one or more of the composite images described herein; combining the pixels in one or more of the composite images with pixels at a same relative position in other composite images to generate a template image of the wells, wherein the composite pixels at the same relative positions represent anticipated positions of printed features in a test plate; and using the template image to find a location of a feature within the test plate, wherein the location indicates presence and amount of a substance in the test plate.

In another aspect, this overlay methods can also be used on images that do not have enhanced dynamic range as described herein. In another aspect, the overlay methods comprise obtaining multiple pixel images representing light intensity output from one or more assays, wherein the wells include features printed in the wells of a testing substrate; combining the multiple pixel images with pixels at a same relative position in other images to generate a template image of the wells, wherein pixels of the template image at the same relative positions represent anticipated positions of printed features in a test plate; and using the template image to find a location of a feature within the test plate, wherein the location indicates a presence and an amount of a substance in the test plate.

Figure 5:
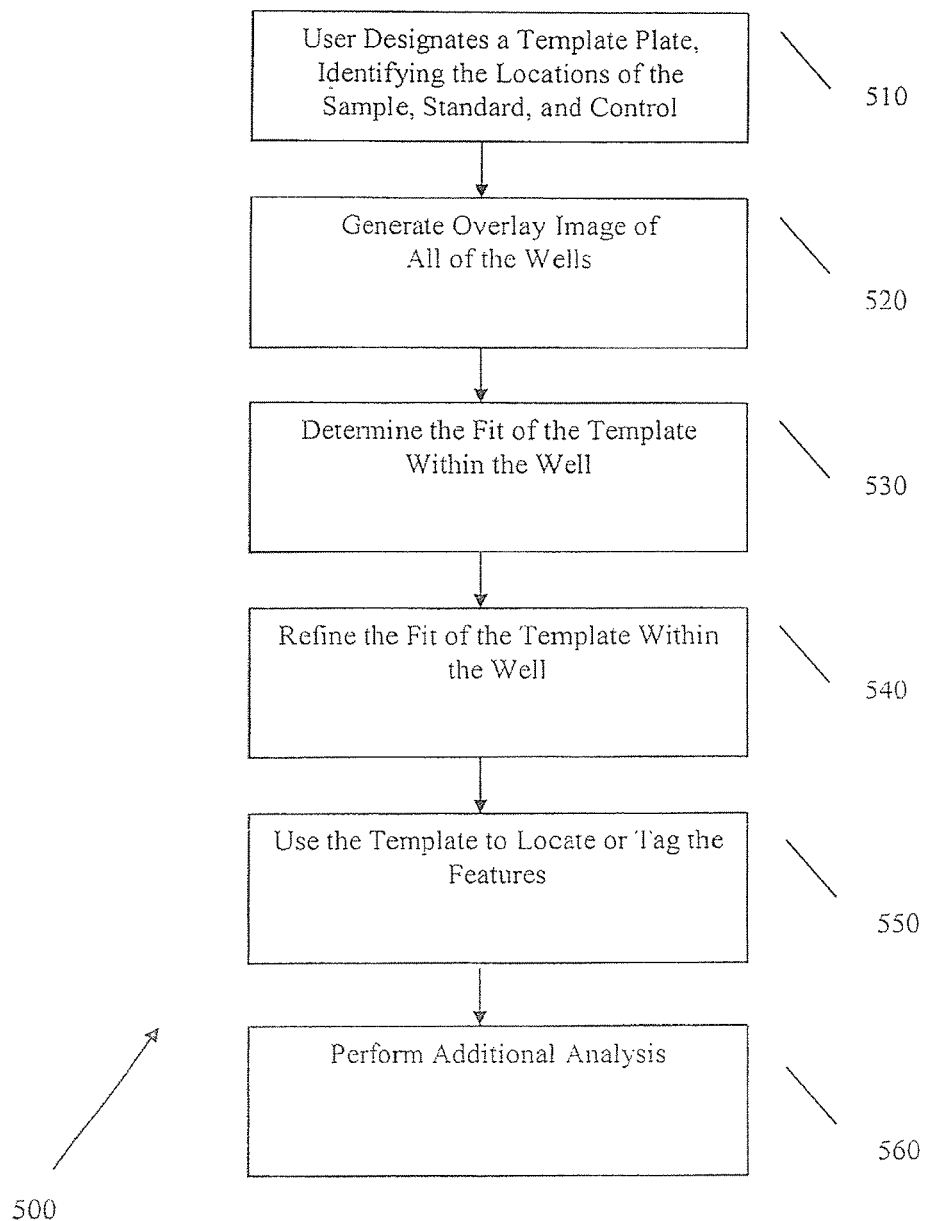
FIG. 5 is a flow chart depicting the sub-steps of step 130 as shown in FIG. 1.

FIG. 5 is a flow chart depicting the sub-steps of step 130 as shown in FIG. 1. In one embodiment, sub-step 510 is performed where a user designates a template plate, where the locations of the sample, standard, and control within the reaction wells are identified. The selection can be made through a user interface to the processing system. Next, in one embodiment, sub-step 520 is performed when the pixels at the same relative positions in each reaction well are summed to generate an overlay image of all of the wells. In some embodiments, histograms are created to generate this overlay image.

In one embodiment, in sub-step 530, the template of the designate features is fit within the wells. In one embodiment, the template of the designated features is varied for feature spacing and orientations to determine the highest response or best fit to the overlay image of all of the wells. The resulting template orientation, feature spacing, and feature locations define an optimum template of the plate.

In one embodiment, in sub-step 540, the fit of the template within the well is further refined and optimized. In this sub-step, the location of the template within the well is adjusted until the maximum response is reached. This location becomes the base template for the individual well. For example, the features of an assay plate can be printed in a grid, such as a 3×3 grid, within a reaction well. Using the techniques described above, a 3×3 feature template is applied to the image of a well by moving it within a certain range within a small grid of pixels from the base feature. In one embodiment, features are moved up to about ½ of the feature diameter from the original position.

In one embodiment, upon arriving at a best fit between the template and the image information, sub-step 550 is performed where the template is used to locate or tag the features. In other words, the template anchors the user or computer as to where to look in the individual wells to determine the presence and strength of signals within the wells and, thus, to accurately interpret assay results.

In one embodiment, in sub-step 560, additional analyses are performed. In one embodiment, the features designated as standards are used as input to a non-linear fit, for example, to estimate the coefficients of a four-parameter log-log transformation algorithm.

A calibration curve plots the relationship between the assay signal (detector response) and the concentration of standard analytes. For example, serial dilution points can be used to calibrate multiplex immunoassays. With the varying concentrations of the calibration features being known, the features produce detectable signals of varying intensity related to the known concentrations. The standard curve can be compared to the signal of the capture antibody feature binding to the antigen-containing test sample to determine the presence and quantity of the sample antigen.

Inaccuracies can occur when the sample concentrations are calculated, and such inaccuracies are especially problematic at the extreme (lower and upper) ends of the calibration curve. Signal variability, such as fluorescence variability, and well-to-well variability in the separate wells can decrease the accuracy and reliability of test results. The image overlay technique described herein (step 130 of method 100) increases the accuracy and reliability of assay analyses.

According to step 140 of method 100, additional analysis techniques well known in the art can be used to further refine and analyze the assay results.

The specific operational parameters provided above are merely illustrative, and other values are within the scope of this disclosure.

Kits can be made that incorporate the devices described herein along with any combination of related equipment or reagents, including reporter reagents and the software described herein for reading, analyzing, and refining assay results.

The embodiments described herein can be used to analyze the presence of antigens and proteins in a patient, such as a patient having an autoimmune disease, antibodies to viral diseases, antibodies to bacterial diseases, antibodies to allergic reactions, or antibodies to cancers.

The techniques and systems disclosed herein may be implemented as a computer program product for use with a computer system. Such implementations may include a series of computer instructions, or logic, fixed either on a tangible medium, such as a computer readable medium (e.g., a diskette, CD-ROM, ROM, flash memory or fixed disk) or transmittable to a computer system, via a modem or other interface device, such as a communications adapter connected to a network over a medium.

The medium may be either a tangible medium (e.g., optical or analog communications lines) or a medium implemented with wireless techniques (e.g., microwave, infrared or other transmission techniques). The series of computer instructions embodies all or part of the functionality described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The terms and expressions that are employed herein are terms of description and not of limitation. There is no intention in the use of such terms and expressions of excluding the equivalents of the feature shown or described, or portions thereof, it being recognized that various modifications are possible within the scope of the disclosure.

The invention claimed is:

1. A method, comprising:
   (a) obtaining multiple images of pixels representing light intensity output from a chemiluminescent assay, wherein the light intensity output indicates a presence and an amount of a substance within wells of a test plate, and wherein the multiple images of pixels are generated by using a detector to detect the light intensity of the pixels of the wells using:
      a standard exposure time; and
      a longer-than-standard exposure time; and
   (b) generating a composite image using the multiple images of pixels, including:
      determining an exposure compensation ratio based on the standard exposure time and the longer-than-standard exposure time;
      determining a presence of out-of-range pixels in the image that used the longer-than-standard exposure time, wherein the out-of-range pixels have light intensities that exceed a threshold based on a maximum capacity of the detector;
      placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio;
      determining a presence of in-range pixels in the image that used a longer-than-standard exposure time, wherein the in-range pixels have light intensities that are below the threshold; and placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

2. The method of claim 1, further comprising:

using the composite image to determine the presence and the amount of the substance within the wells.

3. The method of claim 1 or claim 2, wherein the longer-than-standard exposure time is about 2 to about 10 times the standard exposure time.

4. The method of claim 3, further comprising:

applying an image calibration procedure to the multiple images of pixels generated in step (a), wherein the image calibration procedure includes subtracting dark noise and applying flat field correction.

5. The method of claim 3, further comprising:

obtaining one or more of the composite images;

combining the pixels in one or more of the composite images with pixels at a same relative position in other composite images to generate a template image of the wells, wherein the composite pixels at the same relative positions represent anticipated positions of printed features in a test plate; and using the template image to find a location of a feature within the test plate, wherein the location indicates presence and amount of a substance in the test plate.

6. A method, comprising:

obtaining multiple pixel images representing light intensity output from one or more chemiluminescent assays, wherein wells of a testing substrate include features printed in the wells;

combining the multiple pixel images with pixels at a same relative position in other images to generate a template image of the wells, wherein pixels of the template image at the same relative positions represent anticipated positions of printed features in a test plate; and using the template image to find a location of a feature within the test plate, wherein the location indicates a presence and an amount of a substance in the test plate.

7. A system, comprising:

an image detector;

a timer for tracking exposure time of the image detector; and computer readable medium, including instructions that when executed cause a computer system to generate a composite image using the multiple images of pixels by:

(a) obtaining multiple images of pixels representing light intensity output from a chemiluminescent assay, wherein the light intensity output indicates a presence and an amount of a substance within wells of a test plate, and wherein the multiple images of pixels are generated by using a detector to detect the light intensity of the pixels of the wells using:

a standard exposure time; and a longer-than-standard exposure time; and (b) generating a composite image using the multiple images of pixels, including:

determining an exposure compensation ratio based on the standard exposure time and the longer-than-standard exposure time;

determining a presence of out-of-range pixels in the image that used the longer-than-standard exposure time, wherein the out-of-range pixels have light intensities that exceed a threshold based on a maximum capacity of the detector;

placing out-of-range pixels in the composite image at a same relative position as the out-of-range pixels occurred in the image that used the longer-than-standard exposure time, wherein the light intensities of the out-of-range pixels are based on the light intensities from the image that used the standard exposure time and the exposure compensation ratio;

determining a presence of in-range pixels in the image that used a longer-than-standard exposure time, wherein the in-range pixels have light intensities that are below the threshold; and placing in-range pixels in the composite image at a same relative position as said in-range pixels occurred in the image that used the longer-than-standard exposure time, wherein the light intensities of said in-range pixels are based on the light intensities from the image that used the longer-than-standard exposure time adjusted for light intensity decay due to a passage of time between the image that used the standard exposure time and the image that used the longer-than-standard exposure time.

8. The system of claim 7, wherein the composite image is used to determine the presence and amount of the substance within the wells.

9. The system of claim 7 or claim 8, wherein the longer-than-standard exposure time is about 2 to about 10 times the standard exposure time.

10. The system of claim 9, wherein the multiple images of pixels are processed using a calibration procedure, including subtracting dark noise and applying flat field correction.

* * * * *